United States Patent [19]
Reiss et al.

[11] 3,957,888
[45] May 18, 1976

[54] PROCESS FOR THE MANUFACTURE OF BUTYNEDIOL

[75] Inventors: Wolfgang Reiss, Ludwigshafen; Rudolf Schnur, Frankenthal; Siegfried Winderl, Heidelberg-Wieblingen; Herwig Hoffmann, Frankenthal; Peter Zehner, Ludwigshafen, all of Germany

[73] Assignee: BASF Aktiengesellschaft, Ludwigshafen (Rhine), Germany

[22] Filed: Apr. 18, 1975

[21] Appl. No.: 569,216

[30] Foreign Application Priority Data
May 3, 1974 Germany................................ 2421407

[52] U.S. Cl............................ 260/635 Y; 260/638 Y
[51] Int. Cl.$^2$........................................ C07C 29/00
[58] Field of Search................................ 260/635 Y

[56] References Cited
UNITED STATES PATENTS

| | | | |
|---|---|---|---|
| 2,487,006 | 11/1949 | Walker et al. | 260/635 Y |
| 2,712,560 | 7/1955 | McKinley et al. | 260/635 Y |
| 3,723,545 | 3/1973 | Nagel et al. | 260/635 Y |
| 3,755,469 | 8/1973 | Pasedach et al. | 260/635 Y |

FOREIGN PATENTS OR APPLICATIONS

| | | | |
|---|---|---|---|
| 698,019 | 10/1953 | United Kingdom | 260/635 Y |

Primary Examiner—Joseph E. Evans
Attorney, Agent, or Firm—Johnston, Keil, Thompson & Shurtleff

[57] ABSTRACT

Process for the manufacture of butynediol-1,4 from acetylene and formaldehyde in aqueous solution in contact with a copper acetylide catalyst in the absence of a gas phase.

4 Claims, 1 Drawing Figure

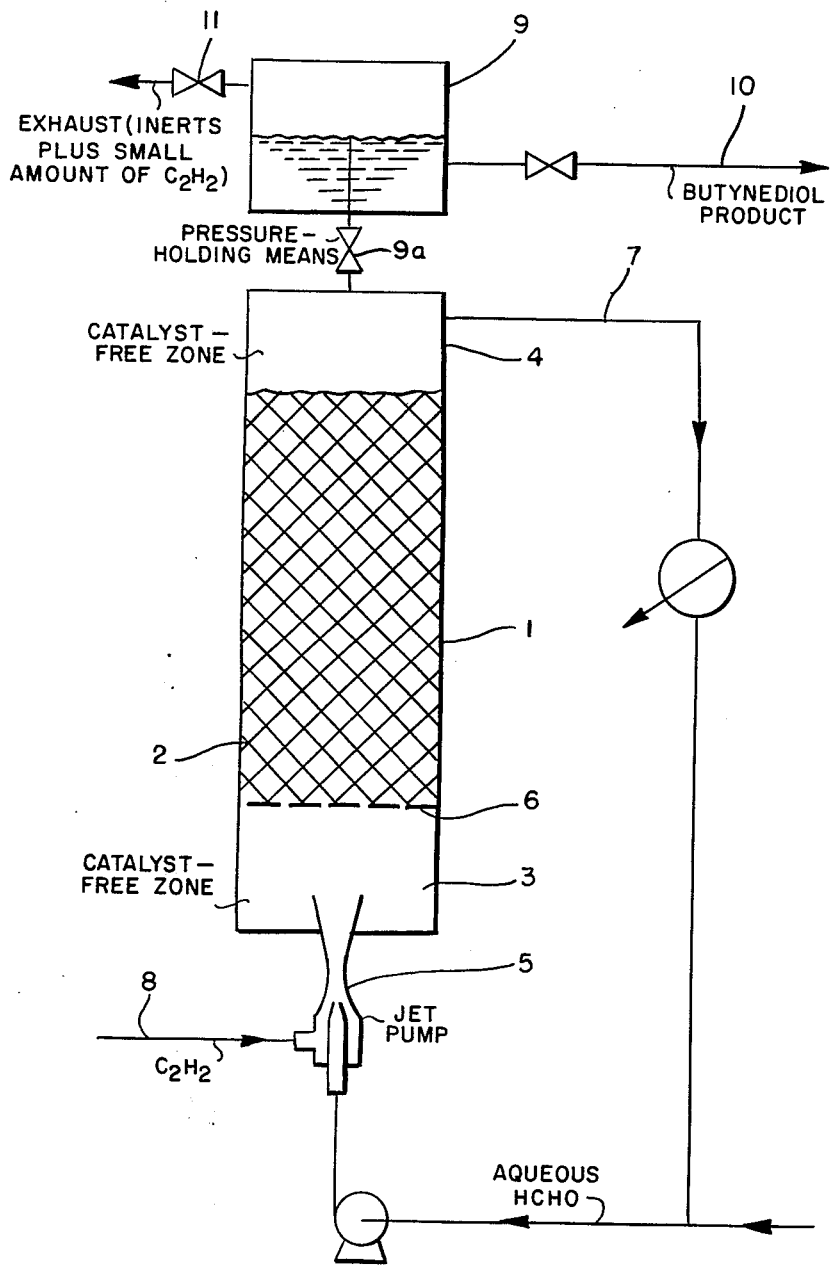

PROCESS FOR THE MANUFACTURE OF BUTYNEDIOL

This invention relates to an improved process for the manufacture of butynediol by reacting acetylene and aqueous formaldehyde solution in the presence of catalysts containing copper acetylide, the catalyst being suspended in the solution or disposed in a fixed position in the reaction chamber, the reaction being carried out at atmospheric or elevated pressure and the formation of a coherent gas phase in the reaction room being avoided.

Although known for a long time (German Pat. No. 725,326), this process suffers from a variety of drawbacks, one of which is the danger involved in using gaseous acetylene, this making it necessary, of course, to undertake costly safety precautions, for example to design the apparatus to withstand more than 10 times the operating pressure (W. Reppe, Chemie und Technik der Acetylen-Druck-Reaktionen, published by Verlag Chemie GmbH, Weinheim, 1951, pages 27 et seq.). Another drawback is the influence of the heat effect of the process on the catalyst when the latter is no longer completely covered by liquid or when, at high conversion rates, the catalyst can only be maintained at low temperatures by very large amounts of liquid.

Thus attempts have already been made to cause a fine distribution of the gas phase in the reaction chamber and to effect even wetting of the catalyst (which in this case is in the form of a fixed bed), as described for example in German Published Application No. 1,040,501. According to this proposal, the liquid and gaseous reactants flow through the fixed catalyst bed concurrently at a considerable velocity, the gas phase being broken up into individual bubbles. The process involves technical problems. On the one hand, it has not yet been possible to develop catalysts which are both highly active and of adequate mechanical strength. The highly fluctuating hydrodynamic stress applied to the catalyst by the two-phase mixture must of necessity cause attrition of the catalysts presently used, such as catalysts of heavy metal acetylide supported on silica gel, aluminum oxide, kaolin, pumice or similar low-strength materials.

On the other hand, although the said process has been improved to a certain extent, it is still not possible to prevent individual gas bubbles from becoming attached to the catalyst surface or even from forming larger coherent volumes of gas, which means that with such an exothermic reaction hot spots occur at such points on account of the reduced heat removal. This undesirable effect leads to a reduction in the catalyst activity and to agglomeration of relatively large portions of the bed.

The aforementioned attrition and agglomeration of the catalyst granules cause a rapid increase in the pressure loss across the bed and, consequently, the catalyst must frequently be replaced for mechanical reasons before it has become inactive.

Another drawback of the above process is that the existence of relatively large coherent columes of gas necessitates the use of a reactor system which is explosion-proof, i.e. capable of withstanding a pressure which is twelve times the operating pressure, as has been pointed out in the introduction.

The disadvantage of explosion-proof and thus very expensive apparatus is avoided by the fluidized bed process described, for example, in German Published Application No. 1,804,696, but the gas bubbles occurring in such a process cause a high degree of backmixing of the liquid, which reduces the reactor output, and also cause increased catalyst attrition. These and other processes requiring the use of very fine particulate catalyst (particle size less than 0.1 mm) have not been adopted on account of serious technical difficulties involved.

Another proposal, which has not yet been adopted industrially, relates to the use of a process in which the formation of a gas phase in the reaction chamber is avoided completely. However, this is only possible if use is made of a better solvent for acetylene than water, for example acetone or tetrahydrofuran, and the operating pressure is extremely high, i.e. from 70 to 140 atmospheres, as described in U.S. Pat. No. 2,712,560.

The proposal made in German Pat. No. 927,687 has also remained of no practical value. According to this proposal, the liquid is not fed to the top of the reactor, i.e. using the principle of irrigation, but is passed to the bottom thereof, acetylene also being blown into the reaction chamber from the bottom. However, the reaction chamber is not completely filled with liquid by this method, as the said patent will appear to disclose, but the operating pressure is maintained by the acetylene so that coherent volumes of gas within the reaction chamber must form. In any case, the drawbacks involved in the use of gaseous acetylene under pressure are not obviated by this method.

We have now found that the problem of carrying out a process of the above kind in the absence of a coherent gas phase may be satisfactorily solved even when the solvent used is water or aqueous formaldehyde solution.

It is an object of the invention to provide an improved process for the production of butynediol from acetylene and formaldehyde in aqueous solution without danger of explosion. It is another object of the invention to provide such a process which is not bound by safety specifications relating to the reaction chambers, i.e. chambers capable of withstanding about ten to twelve times the operating pressure.

These and other objects and advantages are achieved by reacting acetylene and aqueous formaldehyde in the presence of a copper acetylide catalyst in a reaction chamber designed to be completely free from any gas phase, acetylene being fed thereto in aqueous solution.

In order that the reaction chamber may be completely filled with liquid, it is necessary to provide liquid withdrawal means at the uppermost point of the chamber. This measure is advantageously combined with pressure-holding means, as explained below. It is of course necessary to avoid, in the reaction chamber, the formation of cavities in which gases could collect.

The solution to be reacted is advantageously mixed with acetylene immediately before entering the reaction chamber, the amount of acetylene used being, for example, from 0.1 to 1 times the saturation concentration in the particular solution. The solution to be reacted may in this case also be the recycle liquid still containing formaldehyde and having a depleted concentration of acetylene. Mixing of acetylene and aqueous solution may be effected in a suitable chamber upstream of the reaction vessel in the absence of catalyst. A convenient arrangement is discussed below.

It is advantageous, in the present process, to use elevated pressure. Since there is no coherent gaseous acetylene phase, the normal simple safety precautions are sufficient. Consequently, higher reaction rates are possible and the advantages of operating under pressure can be fully exploited. Since, as mentioned above, the process proceeds in the absence of a coherent gaseous phase and thus no hazard is involved, the pressure used has no upper limit; for example, it may be from 1 to 50 bars. However, an adequate reaction rate is generally achieved using a pressure of from 1.5 to 25 bars. In this range, the reaction rate is, as is well known, approximately proportional to the square root of the acetylene concentration. The acetylene concentration in the liquid feed may be adjusted, in industrial plant, at an adequate rate by keeping the partial pressure of the acetylene lower than the reaction pressure, in particular at a value of from 0.1 to 0.95 times the reaction pressure. The temperature at which the reaction is carried out is that generally used, for example from 60° to 100°C.

By a "coherent gas phase" we mean a volume of gas within the reaction chamber which is greater than a few discrete bubbles and exceeds a total of, say, 10 to 1000 milliliters per cubic meter of reaction volume. It is to be understood that the normal impurities in gaseous acetylene, e.g. nitrogen, which are not completely absorbed in the reaction mixture, will normally form more or less microscopic bubbles in this range.

Suitable catalyst are the copper acetylide catalysts suitable for so-called ethinylation according to Reppe. These are described, for example, in German Pat. Nos. 725,326; 726,714; 740,514; 1,103,279; 1,072,985 and 1,075,593, Swiss Pat. No. 220,204, U.K. Pat. Nos. 784,638 and 805,861 and French Pat. No. 1,144,265.

The object of the process of the invention is to avoid the drawbacks which occur in conventional processes by the use of a two-phase feed. This is achieved by causing a single-phase reactor liquid to pass through a fixed or fluidized catalyst bed. This may be most simply achieved by recycling the liquid at a suitable rate so that the amount of acetylene required for the chemical reaction is fed, completely absorbed, to the reactor without the formation of gas bubbles. Absorption of the acetylene may be effected either in separate gas-liquid contacting apparatus or in a catalyst-free chamber of the reactor situated upstream of the catalyst zone.

In the latter case, the acetylene should be introduced in the form of finely dispersed bubbles in large quantities. Such masses of bubbles may be very simply produced using jet pumps (ejectors) in which the gas is drawn in, compressed and, to a major extent, dissolved. The power consumption is low, since the said simultaneous compression and absorption of the gas means that only that portion of the gas has to be pump-compressed to the higher reactor pressure which has not already been dissolved in the jet pump. Thus this method avoids the formation of coherent gas volumes prone to ignition and decomposition, and consequently it is not necessary to use an explosion-proof reactor even at operating pressures above 1.4 bar, i.e. above the safety limit with respect to the spontaneous decomposition of acetylene. However, the use of operating pressures above 1.4 bar allows higher acetylene concentrations in the liquid phase and thus higher space time yields to be achieved.

Where the single-phase liquid passes through a fluidized bed, the effect of a high average acetylene concentration in the liquid as compared with the use of a two-phase mixture passing through a fluidized bed is maintained by the low degree of acetylene backmixing which occurs. For it is found that the macroturbulence caused by the gas bubbles of two-phase feeds through a fluidized bed no longer occur in the process of the invention, which means that backmixing and catalyst attrition are greatly reduced. Furthermore, when a fixed catalyst bed is used in conjunction with a single-phase feed, the catalyst may be used for much longer on-stream periods, since the pressure losses are much less than occur with two-phase feeds, i.e. lower mechanical stresses occur. Moreover, the fact that liquid completely fills all gaps between the particles of catalyst in the bed completely obviates the occurrence of hot spots in the bed.

The process may be advantageously carried out using the apparatus described below with reference to the accompanying drawing.

The reaction chamber 1, which may be filled with a fixed or fluidized catalyst bed, is situated in the reactor 2. Above and below the reaction chamber 1 there are catalyst-free liquid chambers 4 and 3 respectively. The lower chamber 3, which in the present example accommodates a jet pump 5 acting as saturator, is mainly intended to effect complete dissolution of any acetylene bubbles still present and is separated from the catalyst bed 1 by a grate or screen 6. The pressure in the reaction chamber 1 and chambers 3 and 4 is essentially the same, i.e. disregarding the hydrostatic pressure involved. The amount of acetylene fed to the jet pump 5 is controlled such that not more acetylene is applied than is soluble in the liquid feed at the pressure used and the temperature of the liquid feed. Such control is facilitated by the fact that the performance characteristics of the jet pump 5 change with increasing saturation so as to reduce the amount of acetylene drawn in.

Catalyst-free liquid is withdrawn from chamber 4 to the loop 7 which contains only a low concentration of acetylene and is replenished in the jet pump 5 by the fresh gas drawn in from line 8.

The separator 9 is provided for the removal of inert gases from the liquid discharge 10 at a pressure which is below that in the reaction chamber (as controlled by pressure-holding means 9a) such that only very little acetylene is lost through the exhaust 11. It is thus no longer necessary to wash the off-gases for the recovery of acetylene, as is normally required in prior art processes.

In the present embodiment, the reactor liquid passes upwardly through the reactor. However, it is possible to interchange the elements 5 and 7 and thus cause the liquid to flow down through the reactor, since it is possible, by selecting suitable operating conditions, to effect total absorption not only of the acetylene supplied but also of the inert gases, with the result that no more bubbles occur. This means that catalyst particles may be used which are less dense than the reactor liquid, thus opening up a new range of supporting substances for the heavy metal acetylide. Such a possibility holds both for a fixed and for a fluidized catalyst bed. In the latter case the fluidized bed will be situated below a screen.

The advantage of the present invention, which consists, inter alia, in a relatively long catalyst life, is explained below with reference to two examples. The quantities given are by weight, unless otherwise stated.

EXAMPLE

An aqueous formaldehyde solution is reacted with acetylene in apparatus having a cylindrical reaction chamber of 288 mm in diameter and having a height of 10 m, this being filled with a fixed catalyst having a volume of 0.52 m³. The catalyst has an average particle diameter of about 3 mm and contains 12% of copper in the form of copper acetylide and 3% of bismuth, calculated as bismuth oxide, supported on silicon dioxide. The operating pressure is 5 bars. The liquid phase is passed upwardly through the reactor under an acetylene partial pressure of 3 bars. Using a reaction temperature of 90°C at a pH of 5.8 and a feed rate of 80 kg/hr of 30% formaldehyde, the discharged liquid has a butynediol content of 25.3%. The concentration of residue and propargyl alcohol is not significantly different from that in the following Comparative Example. To achieve compression and absorption of 6.2 m³ (STP)/hr of acetylene, reactor liquid must be pumped through the jet pump used at a rate of 4.3 m³/hr, this being equivalent to a liquid throughput of 66 m³/m².hr. The pressure loss across the bed is less than 0.1 bar. Decompression of the discharged liquid to an absolute pressure of 3 bars gives an off-gas having an acetylene concentration of only 6.7% (i.e. 93.3% of inert gas) which means that it is no longer necessary to work up the off-gas in industrial plant, as required in the Comparative Example. The catalyst activity and pressure loss remain unchanged over a test period of three months.

COMPARATIVE EXAMPLE

The reactor described in the Example above is used and liquid and gas are simultaneously passed down through the reactor by the method described in German Published Application No. 2,040,501.

Using a continuous feed of 80 kg/hr of 30% formaldehyde solution at a reaction temperature of 90°C, an average reactor pressure of 5 bars and a pH of 5.8 in the withdrawn reaction mixture, maintained constant by the addition of caustic soda, there is obtained a formaldehyde content of 10.3%, a butynediol content of 24.5%, a propargyl alcohol content of 0.4% and a non-distillable residue of 0.5%. Acetylene is continuously fed to the gascirculation system at a rate of 6.6 m³ (STP)/hr, of which 6 m³ (STP)/hr are consumed in the reaction. To remove the inert gas portions, about 0.6 m³ (STP)/hr of acetylene containing 11% of inert gases must be removed and then washed for recovery of the acetylene.

To ensure that the catalyst bed is evenly supplied with liquid and gas in this method, it is necessary by suitable recycling to maintain a liquid throughput of 60 m³/m².hr and to adjust the gas throughput also to 60 m³/m².hr. The pressure loss across the bed is 0.5 bar when the catalyst is fresh but rises to 3 bars after an on-stream period of about 2 months, this necessitating replacement of the catalyst.

We claim:

1. An improved process for the continuous production of butynediol by reaction of acetylene and formaldehyde in aqueous solution in the presence of a catalyst containing copper acetylide, the catalyst being contained in a reaction vessel in the form of a suspension or a fixed bed at a pressure of from atmospheric to about 50 bars and a temperature of from about 60° to about 100°C, the improvement consisting in mixing gaseous acetylene and aqueous formaldehyde outside the reaction vessel or at its inlet and passing the mixture into the reaction vessel in the absence of a coherent gas phase, and withdrawing the reaction mixture from said vessel at a point where any gas phase or bubbles formed are removed from the vessel together with the reaction mixture being withdrawn.

2. A process as claimed in claim 1, wherein the partial pressure of the acetylene in the aqueous solution is from 0.1 to 95% of the operating pressure in the reaction chamber.

3. A process as claimed in claim 1, wherein the acetylene is mixed with the aqueous solution by means of a jet pump.

4. A process as claimed in claim 1, wherein the operating pressure is from 1.5 to 25 bars.

* * * * *